(12) United States Patent
Gaziano

(10) Patent No.: US 8,321,244 B2
(45) Date of Patent: Nov. 27, 2012

(54) SOFTWARE SYSTEM FOR AIDING MEDICAL PRACTITIONERS AND THEIR PATIENTS

(75) Inventor: Philip F. Gaziano, Wilbraham, MA (US)

(73) Assignee: Quality Health Ideas, LLC, Wilbraham, MA (US)

( * ) Notice: Subject to any disclaimer, the term of this patent is extended or adjusted under 35 U.S.C. 154(b) by 135 days.

(21) Appl. No.: 12/751,159

(22) Filed: Mar. 31, 2010

(65) Prior Publication Data

US 2010/0280848 A1 Nov. 4, 2010
US 2012/0010903 A9 Jan. 12, 2012

Related U.S. Application Data

(60) Provisional application No. 61/165,575, filed on Apr. 1, 2009.

(51) Int. Cl.
*G06F 19/00* (2011.01)
(52) U.S. Cl. .......................................................... 705/3
(58) Field of Classification Search .................. 705/2, 3
See application file for complete search history.

(56) References Cited

U.S. PATENT DOCUMENTS

| | | | |
|---|---|---|---|
| 2002/0035487 A1 | 3/2002 | Brummel et al. | |
| 2003/0074220 A1* | 4/2003 | Brandt | 705/2 |
| 2003/0120516 A1 | 6/2003 | Perednia | |
| 2004/0199404 A1 | 10/2004 | Ripperger et al. | |
| 2005/0273363 A1 | 12/2005 | Lipscher et al. | |
| 2009/0138284 A1* | 5/2009 | Guadagna et al. | 705/3 |

* cited by examiner

*Primary Examiner* — John Pauls
(74) *Attorney, Agent, or Firm* — Donald S. Holland, Esq.; Holland & Bonzagni, P.C.

(57) ABSTRACT

Applicant has disclosed a software system, preferably run over the Internet on an SQL server, used to prompt care providers to check certain medical conditions based upon: a patient's history from, e.g., prior office visits to a physician's office; and preferably, if appropriate, the patient's history from other sources. Using the system results in more thorough care and enhanced billing. Applicant's software provides a digital (or printed) version of a familiar billing format—the so-called Superbill. Medical conditions of a patient are highlighted to ensure the medical service provider performs the following services during a patient visit: investigates medical conditions of the patient, as prompted by highlights in the Superbill; and exhaustively addresses all the conditions worthy of investigation based on stored patient information. Afterwards, additional data obtained from the visit are entered into the computer system for later use. Since the system is set up on a standard billing format—i.e., the Superbill, the system helps to ensure that the service provider's bills and the paperwork submitted to insurance carriers are accurate and complete.

6 Claims, 14 Drawing Sheets

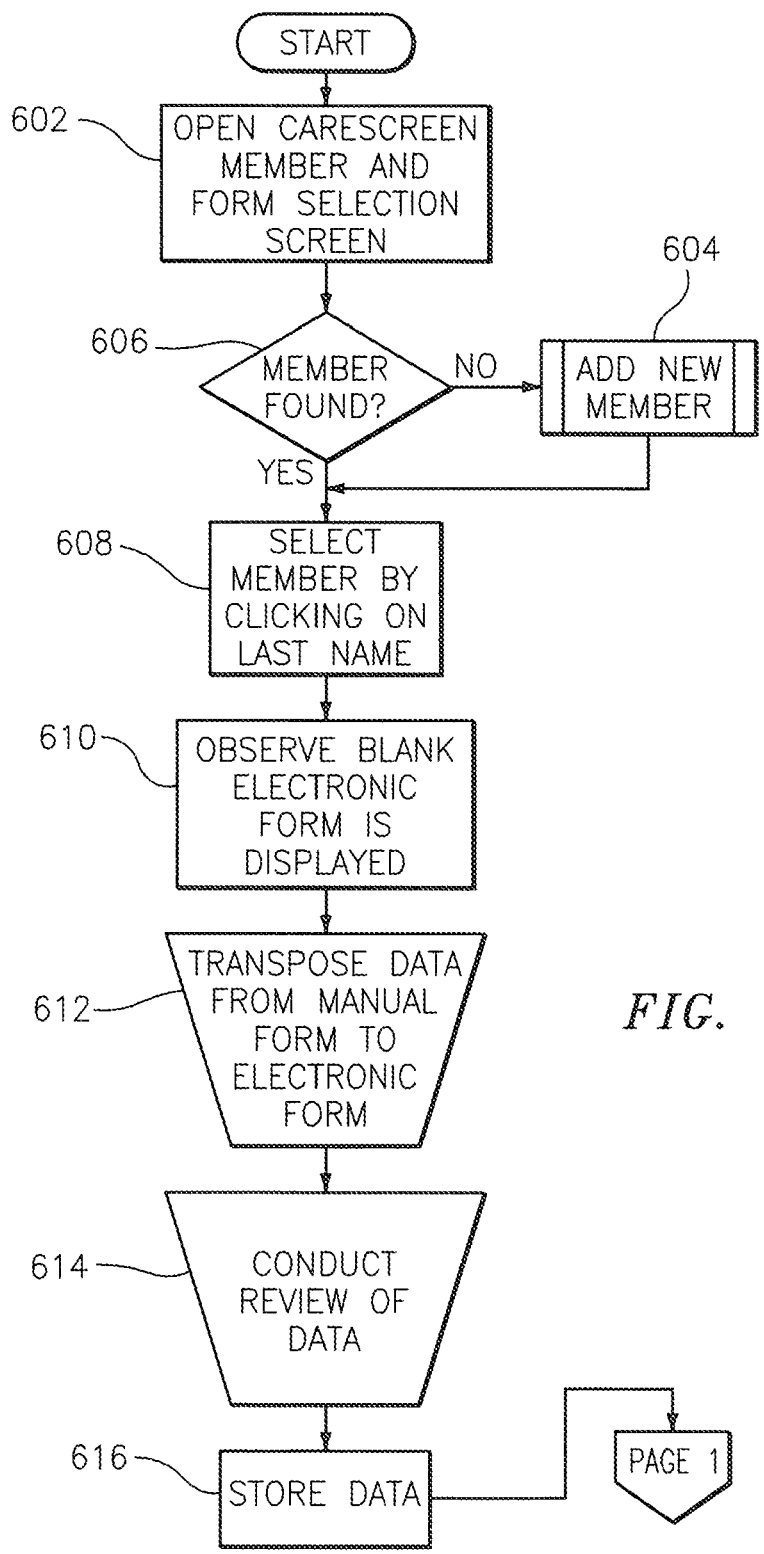

Care Screen Outpatient Encounter Form

DOE, JANE J  
92-F (12-22-1916)  T99999999  
PCP: Phil Gaziano Md  
Tufts-MP-HMO Premium/Rx  
Logged in as Phil Gaziano 3/31/2008  
Case Manager  
Dis. Management Type:   Refer ☑  
Claim Date: 03/31/2008

Tier Recent Rxs./Past 12 mo.

? ??????????????  
? ??????????????  
? ??????????????  
? ??????????????  
? ??????????????  
? ??????????????  
? ??????????????  
? ??????????????  
? ??????????????  
? ??????????????  
? ??????????????  
? ??????????????  
? ??????????????

Health Maintenance Activity

Flu Vaccine: 03-26-08  
Pneumo-Vac: 03-26-08  
Flex Seg:  
Colonoscopy:  
Barium Enema:  
Stool Home Test: 12-08-07  
Glaucoma Screen:  
LDL Screen:  
PSA:  
Hg-A1c: 03-26-08  
Urine Micro-Alb: 03-26-08  
Fasting Glucose:  
Diabetic Eye Exam:  
Osteoporosis Screen:  
Breast Cancer Screen: 11-22-05  
Cervical Cancer Screen:  
Other:  
Other:

Procedures and Tests

| Code | Procedure | Code | Test |
|---|---|---|---|
| ☐ G0008 | Flu Vaccine-Medicare | ☐ V705 | Work Physical |
| ☐ G0009 | Pneumo Vac-Medicare | ☐ V720 | Retina/Eye Exam |
| ☐ G0375 | Smoking Counseling | ☐ V7232 | Pap Exam |
| ☐ 90703 | Tetanus Tozoid | ☐ V7281 | Pre-Op ECG |
| ☐ 90718 | TD Vaccine (Adult) | ☐ V7284 | Pre-Op Evaluation |
| ☐ 90737 | Zoster Vaccine | ☐ V7641 | Rectal Exam |
| ☐ 99241 | Counseling 15 Min. | ☑ V80.1 | Glucose Exam |
| ☐ 99242 | Counseling 30 Min. | ☐ V8281 | Bone Mineral Density |
| ☐ 90772 | IM Injection | ☐ 83036 | HG-A1C |
| ☐ 90780 | IV Infusion | ☐ 81002 | Urinalysis |
| ☐ 95115 | Allergy Injection | ☐ 83042 | Urine Mirco-Albumen |
| ☐ 20600 | Joint Injection | ☐ 82270 | Stool Hemocult (3) |
| ☐ 94010 | Spirometry | ☐ 45330 | Flex Sig. |
| ☐ 94760 | Osimetry | ☐ 87880 | Rapid Strep |
| ☐ 93000 | ECG | ☑ 80061 | Lipid Panel |
| ☐ 93922 | Ankle Brachial Index | ☑ 82962 | FBS |
| ☑ Referred for Colonoscopy | | ☐ 36415 | Venipuncture |
| ☐ Referred for Mammogram | | ☐ 99000 | Lab Handling |

Chronic Co-Morbid Condition Diagnosis

Oncology
- ☐ 174.9 Breast Ca
- ☐ 188.9 Bladder Ca
- ☐ 204.10 CLL
- ☒ 153.9 Colon Ca
- ☐ 150.9 Esophageal Ca
- ☐ 162.9 Lung Ca
- ☐ 202.8 Lymphoma
- ☐ 203.00 Multiple Myeloma
- ☐ 185 Prostate Ca
- ☐ 189.0 Renal Ca

Diabetes
- ☒ 250.70 Diab+Vasc Dis Typ II
- ☐ 250.71 Diab+Vasc Dis Typ I
- ☒ 250.40 Diab+Renal Type II
- ☐ 250.41 Diab+Renal Type I
- ☒ 250.60 Diab+NeuroType II
- ☐ 250.61 Diab+NeuroType I
- ☐ 250.00 Diab Uncompl Type II
- ☐ 250.01 Diab Uncompl Type I
- ☒ 362.02 Diabetic Retinopathy

Renal
- ☐ 583.9 Nephritis
- ☐ 584.9 Acute Renal Failure
- ☐ 585.1 CRF Stg1 (GFR>=90)
- ☐ 585.2 CRF Stg2 (GFR60-89)
- ☐ 585.3 CRF Stg3 (GFR30-59)
- ☐ 585.4 CRF Stg4 (GFR 15-19)
- ☐ 585.5 CRF Stg5 (GFR<15)
- ☒ 585.6 End Stage Failure
- ☒ V45.1 Renal Dialysis Staus

GI & Nutrition
- ☒ 572.3 Portal Hypertension
- ☐ 557.0 Bowel Ischemea
- ☐ 263.9 Protein Malnutrition
- ☐ 456.1 Esophageal Varices
- ☐ 577.0 Pancreatic Diseases
- ☐ 556.9 Ulcerative Colitis
- ☐ 572.8 Chr. Liver Dis. Effects
- ☐ 571.3 Alcohol Liver Dis.
- ☒ 571.5 Cirrhosis Of Liver
- ☐ 799.4 Cachexia
- ☐ V44.3 Colostomy Status

Cardiac
- ☒ 416.0 Pulmonary HTN
- ☐ 416.9 Chronic Pulm Hrt Dis
- ☐ 425.4 1o Cardiomyopathy
- ☐ 425.9 2o Cardiomyopathy
- ☐ 428.0 CHF
- ☐ 428.30 Diastolic Heart Failure
- ☐ 429.0 Myocarditis
- ☒ 413.9 Angina Pectoris
- ☐ 411.1 Int. Coronary Syndrm
- ☐ 410.90 Acute MI
- ☒ 412 Past MI (Recent or Old)
- ☐ 426.0 AV Block Complete
- ☐ 427.0 Arial. Tachycardia
- ☐ 427.1 V. Tachycardia
- ☐ 427.31 A. Fib.
- ☐ 427.32 A. Flutter
- ☐ 427.81 SA Node Dysfunction
- ☐ 427.5 Cardiac Arrest

Vascular
- ☐ 440.1 Renal Art. Dis.
- ☐ 440.21 Limb Claudication
- ☒ 441.4 Abd. Aortic Aneurysm
- ☐ 442.9 Aneurysm (Any)
- ☐ 443.9 Peripheral Vasc. Dis.
- ☐ 447.6 Arteritis
- ☐ 451.19 DVT Leg
- ☐ 451.83 DVT Arm
- ☐ 557.9 Bowel Ischemia

Pulmonary
- ☐ V44.11 Ventilator Status
- ☐ 415.19 PE
- ☒ 496 COPD
- ☐ 492.8 Emphysema
- ☐ 491.9 Chronic Bronchitis
- ☐ 493.20 Chronic Asthma
- ☐ 482.30 Pneumonia (Staph)
- ☐ 507.0 Aspiration Pneumonitis
- ☐ 518.81 Acute Resp. Failure
- ☒ 518.83 Chronic CO2 Retainer
- ☐ 518.4 Pulmonary Edema
- ☒ 799.02 Hypoxia/Cyanosis
- ☐ V44.0 Tracheostomy Status

Psychiatric
- ☐ 303.90 Alcohol Dependence
- ☐ 291.9 Alcoholic Psychosis
- ☐ 292.81 Drug Delirium
- ☐ 295.90 Schizophrenia
- ☐ 297.9 Paranoid State
- ☐ 296.20 Major Depression
- ☒ 296.26 Maj. Deprsn in Remisn
- ☐ 296.80 Bipolar Dis.

Neurological
- ☐ 348.1 Anoxic Brain damage
- ☐ 342.80 Hemiplegia
- ☒ 344.00 Quadriplegia
- ☐ 344.61 Neurogenic Bladder
- ☐ 345.90 Epilepsy
- ☐ 340 Multiple Sclerosis
- ☐ 332.0 Parkinson's Disease
- ☐ 357.2 Neuropathy In Diabetes
- ☐ 357.4 Neuropathy In Other
- ☐ 337.1 Autonomic Neuropathy
- ☐ 359.9 Myopathy
- ☐ 436 CVA/Stroke
- ☐ 780.39 Convulsions
- ☐ 952.9 Spinal Chord Injury

Skin & Bones
- ☐ 707.00 Decubitis Ulcer
- ☒ 707.9 Chronic Skin Ulcer
- ☐ 711.00 Septic Arthritis
- ☐ 730.20 Osteomyelitis
- ☒ 805.6 Vertebral Fracture
- ☐ 808.8 Pelvic Fracture
- ☒ 821.00 Femur Fracture
- ☒ V49.76 AKA Status
- ☐ V49.75 BKA Status
- ☐ V49.73 Foot Amp. Status
- ☐ V49.72 Toe(s) Amp. Status

Autoimmune
- ☐ 279.4 Autoimmune Disease
- ☐ 284.9 Aplastic Anemia
- ☐ 710.0 SLE
- ☐ 714.0 Rheumatoid Arthritis
- ☐ 725 Polymyalgia Rheum.
- ☐ 720.2 Sacroiliitis

Other Diagnoses

Metabolic
- ☐ 278.00 Obesity
- ☐ 272.0 Elevated Cholesterol
- ☐ 272.9 Lipid Metabolic Dis
- ☐ 244.9 Hypothyroidism
- ☐ 281.1 B12 Deficiency
- ☐ 286.9 Coagulopathy

Pain
- ☐ 729.1 Myalgia
- ☐ 719.46 Arthralgia
- ☐ 729.5 Limb Pain
- ☐ 723.1 Neck Pain
- ☐ 724.2 Back Pain
- ☐ 724.3 Sciatica
- ☐ 786.50 Chest Pain
- ☐ 789.00 Abdominal Pain
- ☐ 784.0 Headache

Constitutional
- ☐ 285.9 Anemia
- ☐ 786.05 Dyspnea
- ☐ 780.52 Insomnia
- ☐ 780.79 Malaise & Fatigue
- ☐ 783.21 Weight Loss

ID
- ☐ 79.99 Viral Infection
- ☐ 053.9 Herpes Zoster
- ☐ 382.9 Otitis Media
- ☐ 462 Pharyngitis
- ☐ 465.9 URI
- ☐ 468 Pneumonia
- ☐ 461.9 Acute Sinusitis
- ☐ 466.00 Acute Bronchitis
- ☐ 599.0 UTI
- ☐ 682.9 Cellulitis
- ☐ 786.2 Cough

Cardiovascular
- ☐ 401.1 Benign HTN
- ☐ 401.0 Malignant HTN
- ☐ 424.0 Mitral Valve Dis.
- ☐ 424.1 Aortal Valve Dis.
- ☐ 785.1 Palpitations
- ☐ 780.2 Syncope/Collapse
- ☐ 782.3 Edema

GI
- ☐ 455.6 Hemorrhoids
- ☐ 578.9 GI Bleed
- ☐ 562.11 Diverticulitis
- ☐ 562.10 Diverticulosis
- ☐ 564.1 Irritable Bowel
- ☐ 564.00 Constipation
- ☐ 530.81 GERD
- ☐ 530.11 Reflux Esophagitis
- ☐ 535.50 Gastritis/Duodenitis
- ☐ 787.2 Dysphagia
- ☐ 787.91 Diarrhea

GU
- ☐ 600.00 BPH
- ☐ 607.84 Impotence (Organic)
- ☐ 599.7 Hematuria
- ☐ 788.30 Urinary Incontinence

Reactive
- ☐ 493.90 Acute Asthma
- ☐ 477.9 Allergic Rhinitis
- ☐ 692.9 Dermatitis

Neurological
- ☐ 294.8 Organic Brain Synd.
- ☐ 331.0 Alzheimer's Dis.
- ☐ 389.9 Hearing Loss
- ☐ 435.9 TIA
- ☐ 724.00 Spinal Stenosis
- ☐ 780.93 Memory Loss

Orthopedic
- ☐ 274.9 Gout
- ☐ 354.0 Carpal Tunnel Synd.
- ☐ 733.00 Osteoporosis
- ☐ 715.90 Osteoarthritis (DJD)
- ☐ 716.90 Arthropathy
- ☐ 727.3 Bursitis
- ☐ 726.10 Rotator Cuff Dis.

Other
- ☐ 300.00 Anxiety
- ☐ 305.1 Tobacco Use
- ☐ 365.1 Glaucoma
- ☐ 366.10 Cataract
- ☐ 380.4 Cerumen Impaction
- ☐ 459.81 Venous Insufficiency

Other Past Chronic Diagnoses
- ☐ 141 Malig Neo Tongue*
- ☐ 148.3 Mal Neo Post Hypopharynx
- ☐ 403.91 Hyp Kidney Nos W Chr Kid
- ☐ 585 Chronic Renal Failure

Problem Oriented Visits

| New Primary | Consult | Follow Up |
|---|---|---|
| ○ 99201 | ○ 99241 | ○ 99211 |
| ○ 99202 | ○ 99242 | ○ 99212 |
| ○ 99203 | ○ 99243 | ○ 99213 |
| ○ 99204 | ○ 99244 | ○ 99214 |
| ○ 99205 | ○ 99245 | ○ 99215 |

Well Visits
- ○ 99385 New 18-39
- ○ 99386 New 40-64
- ○ 99387 New 65 Up
- ○ 99395 Est. 18-39
- ○ 99396 Est. 40-64
- ○ 99397 Est. 65 Up

New Diagnoses:
1. [____] 2. [____]

[Back]  [Print]  [Submit]

*FIG. 15*

Encounter Review
Name: DOE, JANE J
Age: 91-F (12-22-1916)
Care Provider: PHIL GAZIANO MD
Encounter Date: 3/26/2008
Location: Primary Office
Encounter Type:

Please Select the Primary Diagnosis for this Encounter
o 153.9    Colon Ca
o 250.70   Diab + Vasc Dis Type II
o 250.40   Diab + Renal Type II
o 250.60   Diab + Noure Type II
o 362.02   Diabetic Retinopathy
o 585.6    End Stage Failure
o V45.1    Renal Dialysis Status
o 263.9    Protein Malnutrition
o 799.4    Cachexia
o 416.0    Pulmonary HTN
o 413.9    Angina Pectoris
o 412      Past MI (Recent or Old)
o 441.4    Abd. Aortic Aneurysm
o 496      COPD
o 518.83   Chronic CO2 Retainer
o 799.02   Hypoxia / Cyanosis
o 296.26   ???
o 357.2    Neuropathy In Diabetes
o 707.9    Chronic Skin Ulcer
o 805.8    Vertebral Fracture
o 821.00   Femur Fracture
o 49.76    AKA Status

[Change Diagnosis]    [Submit Form]

*FIG. 17*

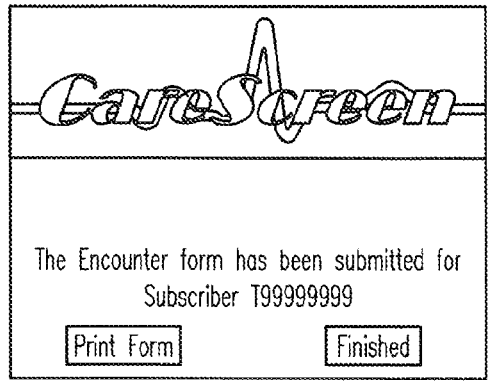

The Encounter form has been submitted for Subscriber T99999999
[Print Form]    [Finished]

3/29/2008                    User Options
Search:                      Change Password
        Last Name            Add User
        First Name           User Maint
        Subscriber #         Reports
                             Log Off
            [Add New]

*FIG. 18*

Change Your Password
Current Password:
New Password:
Confirm New Password:
[Change Password]    [Cancel]

*FIG. 19*

SOFTWARE SYSTEM FOR AIDING MEDICAL PRACTITIONERS AND THEIR PATIENTS

RELATED APPLICATION

This application claims priority from Applicant's U.S. Provisional Patent Application Ser. No. 61/165,575, filed Apr. 1, 2009. Applicant claims the benefit of priority from that provisional application. Applicant also hereby incorporates the disclosure from that earlier application herein by reference.

FIELD OF INVENTION

This invention relates in general to medical record keeping and billings. More particularly, it relates to computerized processes for providing such assistance to medical practitioners and their patients.

BACKGROUND OF THE INVENTION

Medical practitioners see multiple patients daily for a wide variety of problems. Traditionally, records have been kept on paper. Practitioners create records for each patient, or "member" or "client." In smaller offices, records often are kept by hand. Records are filed on a shelf or in a file cabinet and subject to loss or misfiling. Notes concerning office visits, or "encounters" (defined below in the Detailed Description section), may be disorderly within member files. Practitioners reviewing such records while preparing to meet a patient are often pressed for time. Reviewing such records thoroughly on short notice is difficult often leading to cursory reviews and poor follow-up on symptoms. Often, only the very recent past is thoroughly reviewed. There is nothing in the typical system to prompt a practitioner faced with a particular symptom or condition to look for related problems. The practitioner's records often do not contain information on pharmaceuticals and courses of therapy or treatments used by an individual member, particularly if the service was rendered outside the practitioner's office or by another practitioner.

At the conclusion of an encounter, the practitioner typically handwrites or dictates notes concerning the visit and the notes are filed in the member's file. In either case, retrieving the information is done by opening paper files and reading the paper records. This method of recordkeeping is more apt to happen in private practitioners' offices than in hospital settings.

Billing is typically accomplished using what's known as a "Superbill." The Superbill contains a list of possible conditions. The practitioner enters the member's name on the Superbill and proceeds to check off any conditions for which the member was seen. If the practitioner forgets to ask about a related condition during the encounter, that condition cannot be billed. Only conditions actually addressed during the encounter can be placed on the Superbill and submitted for payment.

The present invention is intended to supplement the practitioner's current system by providing a simple, time saving solution to a number of the problems inherent in those systems. The present invention collects and stores practitioner and member data in a remotely located or less often a local secure database. Accessing the database, the practitioner prepares an encounter form to be used during each member visit. The encounter form displays the member's medical history including recent complaints, conditions, medications, tests, and referrals. It also highlights additional conditions that are commonly associated with or related to the member's recent conditions. Thus the system prompts the practitioner to inquire about commonly related subjects ensuring that such items do not go unnoticed and untreated.

The pre-encounter form takes about 15 seconds to produce and saves the practitioner valuable time that otherwise would be spent reviewing manually produced records and prepares the practitioner for the member visit. The pre-encounter form is usually printed for use during the visit, but it can be completed on-line during the visit, and ordinarily can be opened, viewed, and completed from within other existing medical recordkeeping software programs—Electronic Health Records ("EHR") or Electronic Medical Records ("EMR").

During a member's visit, or encounter, the practitioner, places a check mark next to each pre-printed condition addressed during the visit. The highlighted conditions serve to remind the practitioner of previously addressed complaints and those commonly related conditions that should be addressed. The practitioner also notes the primary reason for the visit, and signs and enters the date on the form.

After the office visit, the pre-encounter form is used as an aid in making the post-encounter entries on the appropriate form using the inventive software. Post-encounter entries can be made by the practitioner or by office staff. To make the entries, the user opens the post encounter form on a computer terminal and then fills-in the indicated information according to on-screen instructions. The information collected includes all conditions addressed during the visit, and any medications or follow-up treatments or referrals ordered as a result of the visit. The software stores all of the visit data in the secure server making the data available for future visits. After the post encounter entries are completed, the encounter form is used to ensure billing is accurate for the conditions addressed. Data gathered on many patients is used to determine which patients are worthy of enhanced attention.

Practitioners would normally complete and save their traditional documentation in the usual manner according to their normal office procedures.

SUMMARY OF THE INVENTION

Applicant has disclosed a software system, preferably run over the Internet, to prompt care providers to check certain medical conditions based upon: a patient's history from, for example, prior office visits; and preferably, if appropriate, the patient's history from other sources. Using the system results in more thorough care and enhanced billing.

Applicants's software provides a digital (or printed) version of a familiar billing format—the so-called Superbill. Medical conditions of a patient are highlighted to ensure the medical service provider performs the following services during a patient visit or "encounter": investigates medical conditions of the patient, as prompted by highlights in the Superbill; and exhaustively addresses all the conditions worthy of investigation based on stored patient information. Afterwards, additional data obtained from the visit are entered into the computer system for later use.

Since the system is set up on a standard billing format—i.e., the Superbill, the system helps to ensure that the service provider's bills and the paperwork submitted to insurance carriers are accurate and complete.

Use of Superbills also makes the system easier to learn and to use and improves acceptance by practitioners including those who may have become creatures of habit. The information is stored on a secure and preferably remote database so it is not subject to being lost or destroyed in the confines of the service provider's office.

BRIEF DESCRIPTION OF DRAWINGS

The above and other objects will become more readily apparent when the following description is read in conjunction with the accompanying drawings, in which:

FIG. 6 is a flowchart showing the steps required to store patient information following an encounter;

Figure 9:
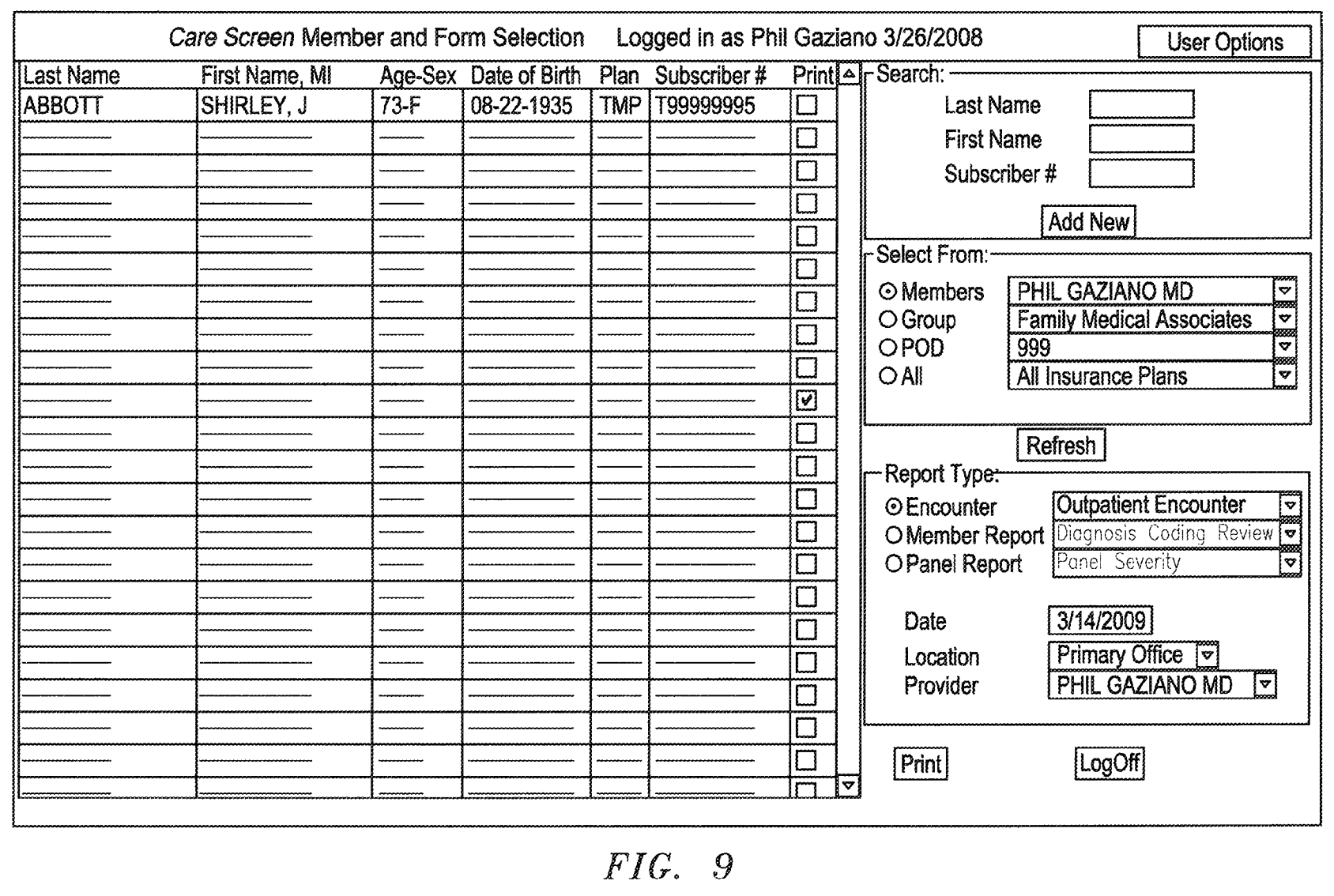

FIG. 9 shows the form used to select patients for printing of encounter forms and for entering visit data. The form also provides functionality for printing various reports;

FIG. 10 shows a form used to select practitioners and groups of patients within which records for patients to be seen will be located;

FIG. 11 shows the same figure as FIG. 10, but with a different radio button selected;

FIG. 12 shows a form used to select different types of reports;

FIG. 14 shows a closer view of the top of an encounter form showing Health Maintenance activity and referral information;

FIG. 15 shows the bottom half of the electronic encounter form;

FIG. 17 shows the encounter review form and a dialog box used to print the form and to complete the saving of patient data to the database;

FIG. 18 displays the dialog box used to select the function needed for changing passwords; and FIG. 19 displays the dialog box used when changing passwords.

DETAILED DESCRIPTION OF THE PREFERRED EMBODIMENT

Applicant has disclosed a software system for use by medical service providers. Quality Health Ideas, LLC, located in Wilbraham, Mass., markets this software system under the trademark "CareScreen."

As used in this application, the term "encounter" means a patient's visit or appointment with a medical professional at any location known for providing medical services, such as a doctor's office or a hospital or an outpatient clinic. Medical professionals include doctors and nurse practitioners.

Figure 13:
FIG. 13 shows an example "encounter form" and identifies features of the form.

In the preferred embodiment, Applicant's system supplies information in a familiar format 10 (see FIG. 13) to doctors, nurse practitioners, and case managers where and when it can do the most good—just before and during an encounter. The preferred system guides the health care provider and enhances patient care by enumerating all conditions that should be examined or considered during a visit. It provides a record of each encounter that improves billing completeness and accuracy and allows for thorough review of billing records. It also collects patient data and allows identification and selection of worthy candidates for managed care. (See generally, FIGS. 1-19.)

CareSereen facilitates use by medical professionals whose offices (or hospitals) use paper and electronic recordkeeping systems alike. For doctors, nurse practitioners, and other medical service providers—"practitioners"—the software generates a one-page "Superbill" (see FIG. 13) just prior to an office visit with a patient. The inventive Superbill contains patient history and a list of conditions to consider based on the patient's history. The system uses information gathered from the patient's previous health care encounters including encounters with other service providers. Data is downloaded to the system from insurance company and hospital databases, and health care association databases and includes data logged using the inventive software. The information is provided on forms printed from computers located in the health care provider's offices. Use of the familiar Superbill format simplifies learning and use of the system.

Because data on many patients is contained in the database, case managers can search for individuals who are in need of managed care or close medical supervision—for example, members whose use of health care services is overly frequent or costly. (See FIG. 18, User Options—Reports.) The need for augmented medical attention is highlighted at the point of treatment and is fresh in the care provider's mind immediately before a patient appears in the office instead of weeks or months in advance. The system is fully HIPPA compliant, housed on a secure server, and it records any access to records by practitioners whether or not associated with a given member.

During an encounter, the health care provider—usually a physician or physician's assistant, places check marks in blocks on the Superbill corresponding to conditions to be evaluated. The Superbill is prepared specifically for the individual receiving care (see FIGS. 13, 14 and 15). It highlights conditions and complaints from past visits and provides for annotating the primary reason for the encounter. The care provider checks-off all conditions examined or investigated during the visit. Following or during an encounter, office personnel input data from the visit into the CareScreen database (see FIGS. 16 and 17).

The Superbill can be used as a record when entering billing information into the provider's billing system. This helps to ensure that the practitioner submits complete billing information to the insurance company or patient. The forms can later be used to audit billing records to ensure all eligible charges were appropriately billed.

The backbone of the inventive software is a Structured Query Language ("SQL") server and the associated hardware, computing, and storage device or devices which can be located at any site or sites having access to the Internet, however, in a less preferable embodiment the system is capable of running on a stand alone computer. The software is comprised of a relational database and several input and output modules. Preferentially, it runs on a remote computer, that is, the program instructions are executed on a centrally located device, but the users typically view and manipulate the software over the Internet using computer terminals located at medical service provider offices, and in the preferred embodiment the only aspect of the software that runs on a user machine is a print applet (not shown) supplied by Microsoft® which is used to print the encounter forms. Those skilled in the art will appreciate what an SQL server is and what a relational database program is and generally how they function to accomplish the tasks described in the following discussion. Program flow is illustrated in the attached flowcharts (see FIGS. 1-6) which may be helpful in determining how the software functions.

Generally, data is organized in the relational database in tables. Each table can be viewed conceptually as having rows and columns. The columns and rows in each table have headings and relevant data is stored in cells at the intersection of appropriate rows and columns. As an example, a table might contain member (or patient, or client) data. Each row would contain data for the member whose member number appears in column one. Other data (called "fields") for each member would include the member's first, middle, and last names, birth date, address, phone number, name of next of kin, and other pertinent information describing the member. Another table might contain member medical diagnoses. The later table would again contain data in rows for each member, and again the first column might contain a member number. Other columns would be headed by the names of various possible conditions and the date upon which such conditions were addressed. Some rows would remain blank or empty under column headings in situations in which a member was never seen for the condition heading for that column. The two tables just described can be "related" to one another by the member number.

Of course there would be numerous other tables each having one or more key columns that would be used to "relate" the table to other tables within the database.

Software modules are written for use within Internet browsers such as Microsoft, Explorer®, Netscape®, or Firefox®, and others, operating on MS Windows®, or other graphical user interface programs and may use any combination of software development tools such as C, C++, Visual Basic®, .NET®, Java®, and others.

As indicated on the flowchart (see FIG. 1) entitled "CareScreen Overall Program Flow," there are several administrative functions that need to be addressed to set up the software (see blocks 102, 104, 106 and 108). The administrative functions are handled by the software vendor as part of the service related to provision of the software and license. The user ordinarily does not own any specific computer hardware or hold copies of the software. The first administrative step is to create the "practice" or "practitioner" or "user"—ordinarily the medical service provider which in most cases is a physician or physician's assistant (see block 104).

One administrative module not shown on the flowchart is a module allowing periodic backup and file maintenance on the database, and modules allowing the user to change passwords (see FIGS. 18 and 19). Files are periodically backed-up by the software vendor to improve the reliability of the system.

Referring to the flowchart (see FIG. 2) entitled "CareScreen Create/Edit/Delete Practice," to create a practice, the administrator first logs-on to the server via a secure encrypted internet connection. The administrator enters a user name and password (see block 202) and is then presented with a blank form containing the pertinent practice information (see blocks 204 and 206). Information required of the practice includes but is not limited to for example the practice name, address, phone number, billing information, and e-mail address. The same software module allows existing practice information to be created, viewed (see block 208), edited (see blocks 210 and 212), and stored in the database and if necessary, deleted (see blocks 214 and 216); afterwards, the user closes the database (see block 218). Once a practice is created, the practice user name and an initial password are given to the medical service provider for its exclusive use. The medical service provider or "practitioner" or office staff changes the password during the initial log-on and thereafter may change the password at any time using another software module (see FIG. 19).

The above modules are controlled and used by the system administrator whereas the modules described below are used by the practitioner or others within the practitioner's office.

A similar module is provided for creating, deleting, editing, and storing an identified patient (or member, or client), and for closing the module. See the "CareScreen Create/Edit/Delete Patient" flowchart in FIG. 3, blocks 302, 304, 306, 308, 310, 312, 314, 316, and 318. Note: As will be appreciated by those skilled in the art, when not being treated, individuals covered under a health care plan are generally referred to as "members," but during the course of examination or treatment they are referred to as "patients."

Figure 1:
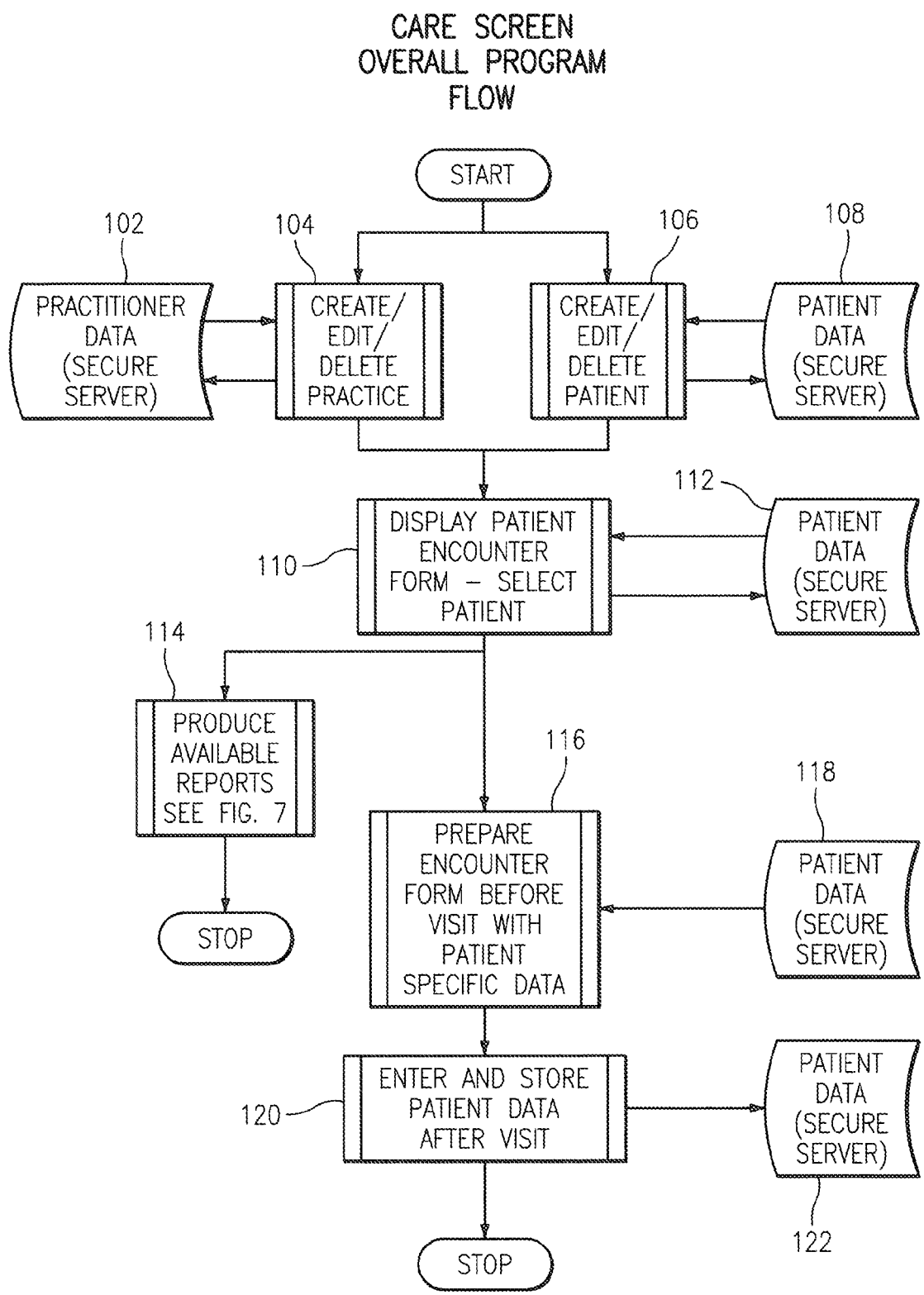
FIG. 1 is a flowchart showing the overall program flow.
Figure 2:
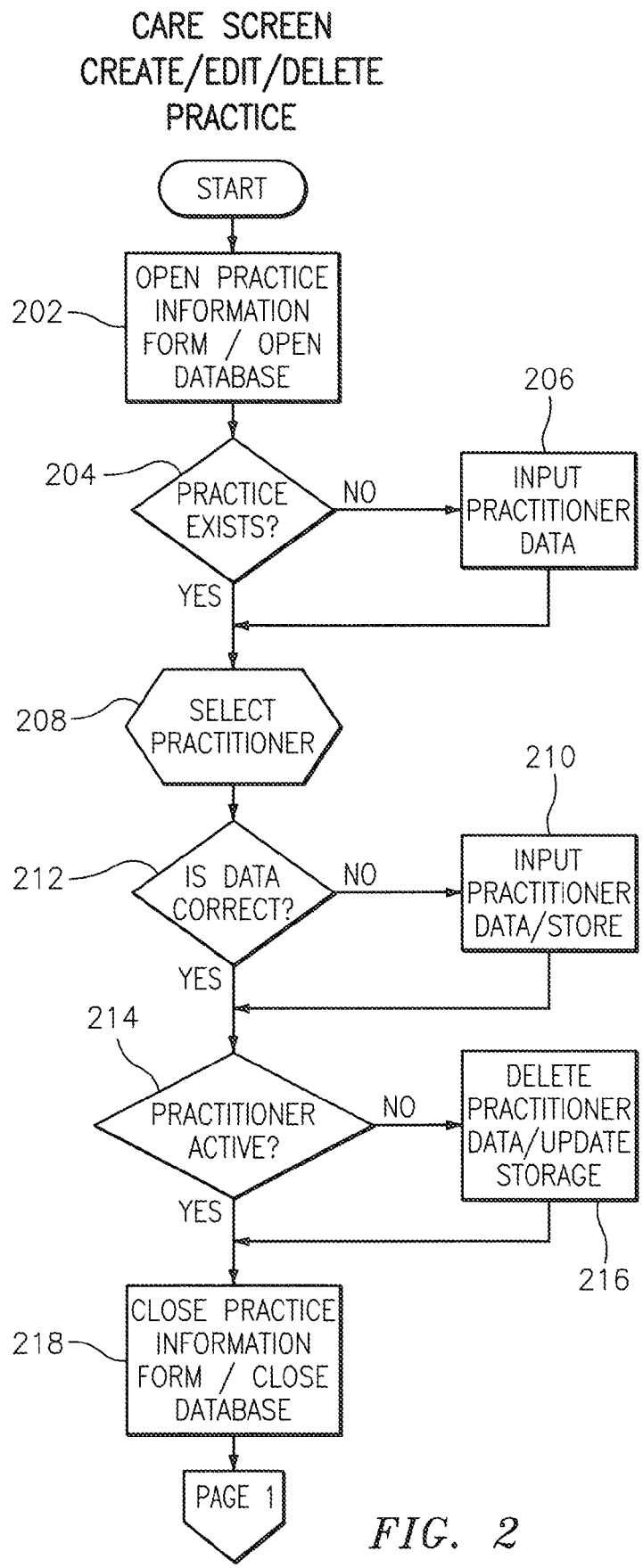
FIG. 2 is a flowchart showing the steps involved in adding, editing, or deleting a practitioner account in the software.
Figure 3:
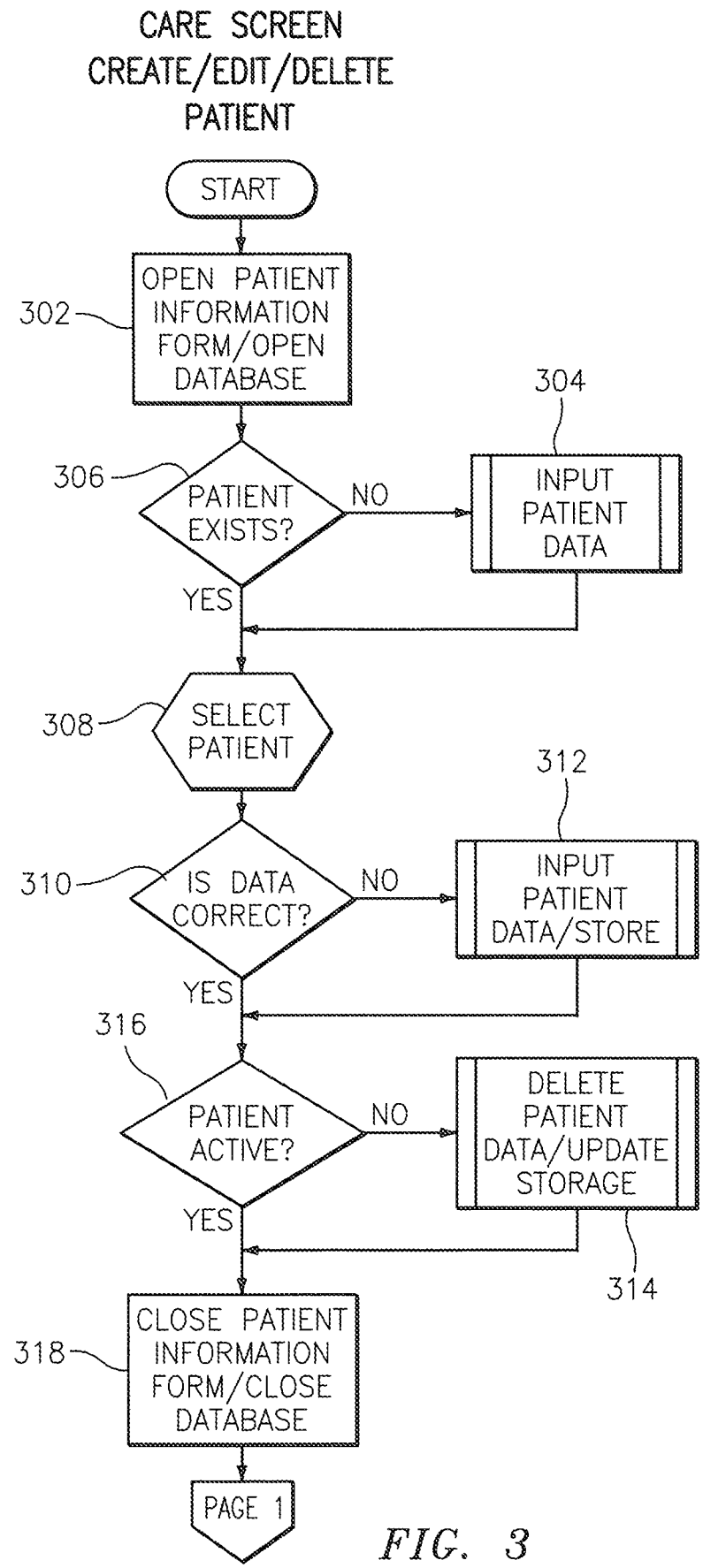
FIG. 3 is a flowchart showing the steps involved in adding, editing, or deleting a patient account in the software.

Attention is drawn to the "CareScreen Overall Program Flow" diagram (see FIG. 1, blocks 110, 112 and 114). After logging in (see FIGS. 7 and 8), the first routine step in the practitioner's process is to display the patient encounter form and select a patient (see block 110). The "CareScreen member selection screen" (see FIG. 9) is used for this purpose and is the means for selecting patients which are also referred to as members. The practitioner prints an encounter form (see FIG. 1, blocks 116 and 118) bearing the member's name and history (FIGS. 14 and 15). The practitioner uses the form as further described below as an aid in performing the examination. Following the examination, the practitioner transfers data collected during the visit to the CareScreen database for later use (see FIG. 1, blocks 120 and 122). The following paragraphs describe these steps in greater detail.

Referring now to the diagram (see FIG. 4) entitled "Display Patient Encounter Form—Select Patient," as the drawings indicate, this is the first routine step in the operation of the inventive software. Once a member has been created by a practitioner (see block 406), the practitioner is ready to receive the member for an office visit or "encounter."

The flowchart (see FIG. 4) entitled "Display Patient Encounter Form—Select Patient" details the steps taken in advance of a visit. Before a member visit, the practitioner opens the "CareScreen member selection screen" (see FIG. 9) and the software displays a list of members from the database for those members associated with the user's practice (see FIG. 4, blocks 402, 404, 406). If the member is found, the user selects the member's encounter form for printing by checking a checkbox (see block 408). If more than one member is visiting, more than one member's box can be checked. If there are too many members to display, scroll bars are displayed allowing the user to move hidden elements of the list into view. To assist the user in locating member's data when the number of members is very high, the software allows for searches using various search and filtration criteria. After selecting one or more members, the user selects "print" (see block 410). An encounter form (see FIGS. 14 and 15) is printed for each selected member showing relevant previously stored data concerning the member including name, age, conditions previously addressed, and any related conditions that might be expected and should therefore be addressed. The encounter form also shows prescriptions filled within the past year (see FIG. 14), and provides space to annotate any tests and procedures, or necessary referrals the member might need (see FIG. 14).

In the most preferred embodiment, the system is capable of drawing on data from outside sources such as member personal electronic medical information cards, and those sources available to insurance carriers, pharmacists, and other service providers.

Figures 10, 11, 12:
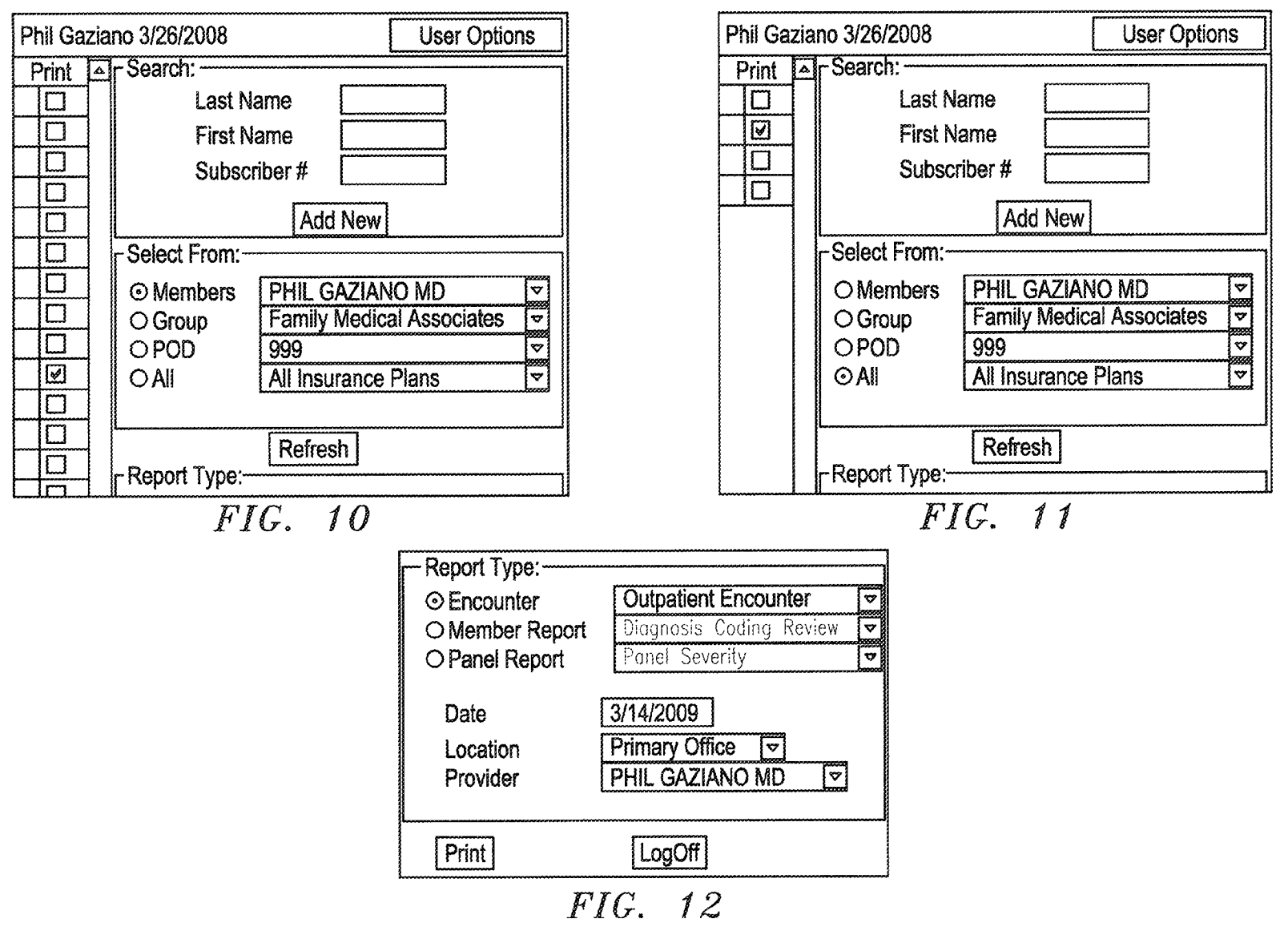

The CareScreen member selection screen (see FIG. 9) also allows the user to select member lists from among those of various practitioners (see FIGS. 10 and 11), and to select from several different report types (see also FIG. 12). The most commonly used report is the encounter form (see FIGS. 14 and 15).

Figure 4:
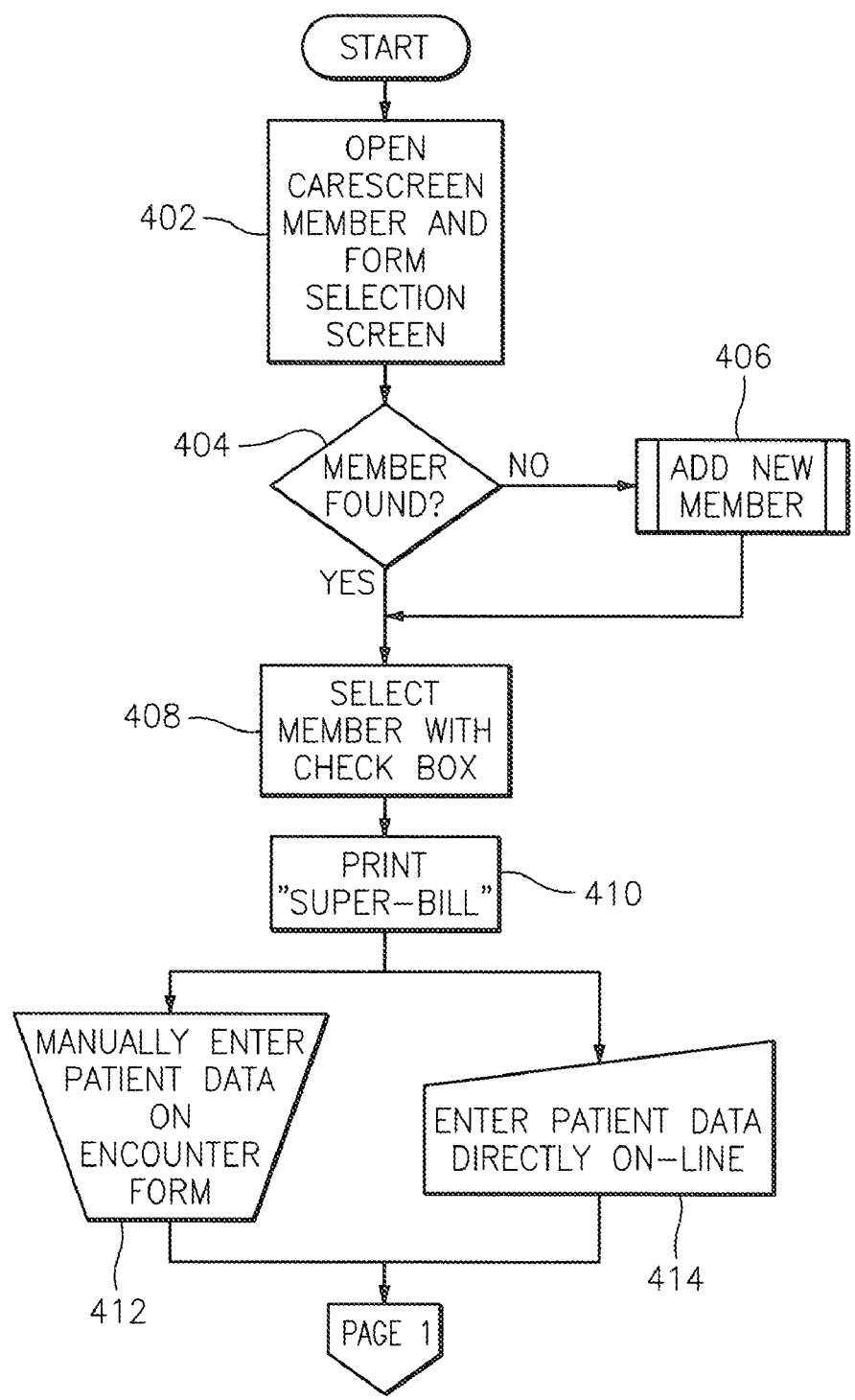
FIG. 4 is a flowchart showing the steps involved in selecting a patient from the data base and displaying or printing the selected patients' encounter form(s)
Figure 5:
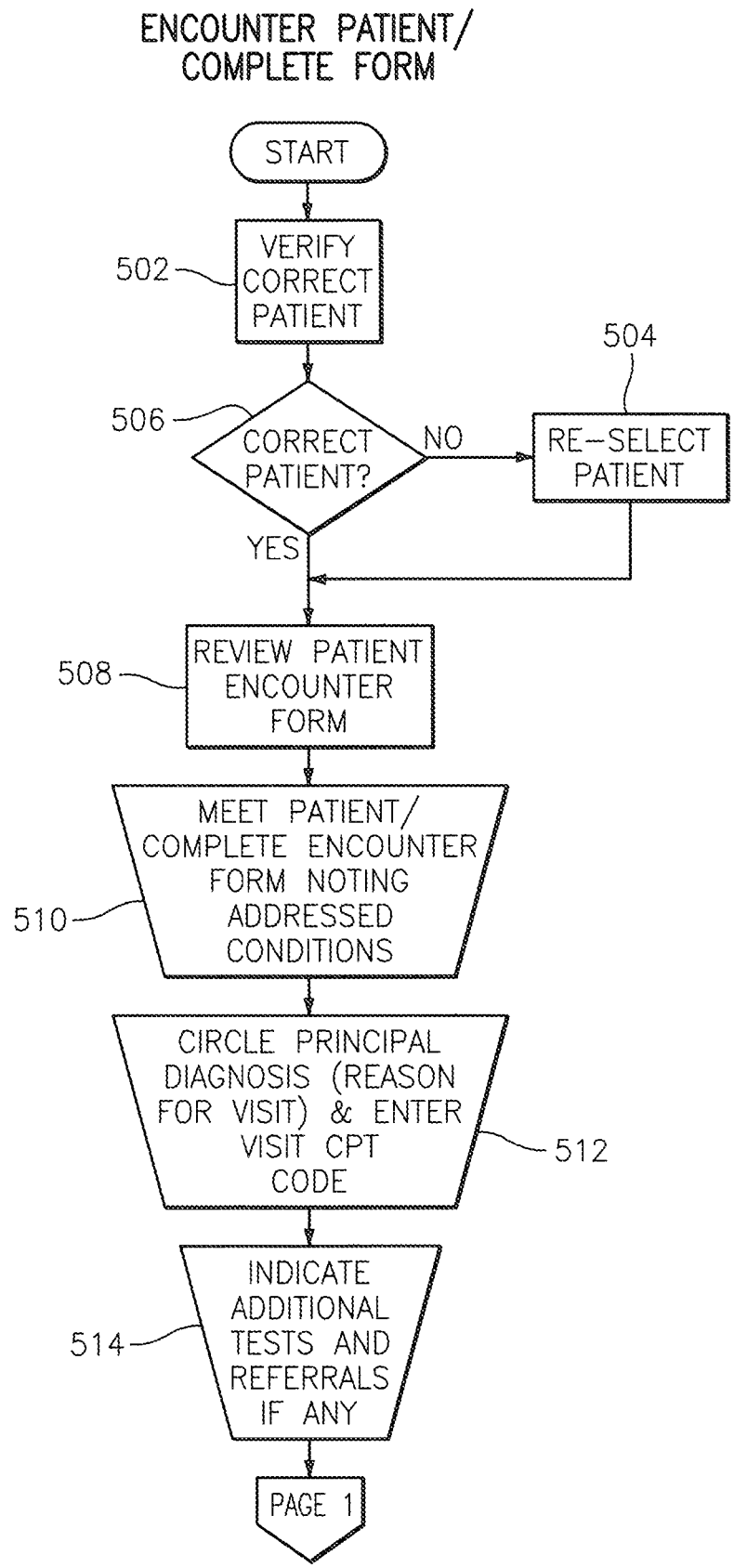
FIG. 5 is a flowchart showing the steps followed by a practitioner during a patient encounter.
Figure 8:
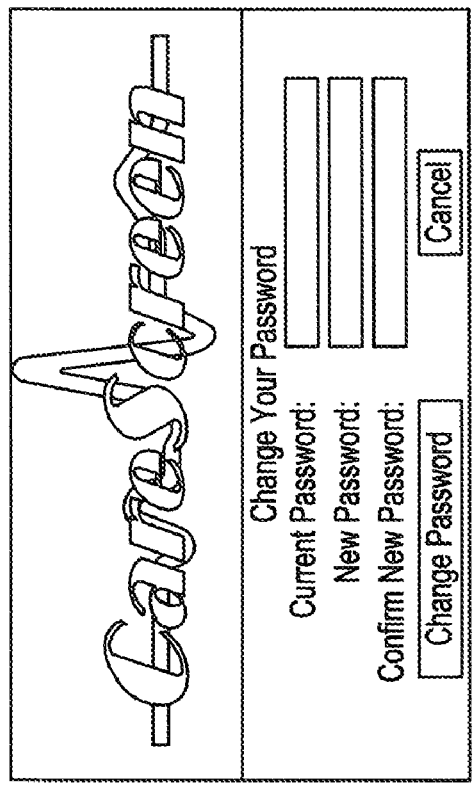
FIG. 8 shows the form used to change passwords.
Figure 7:
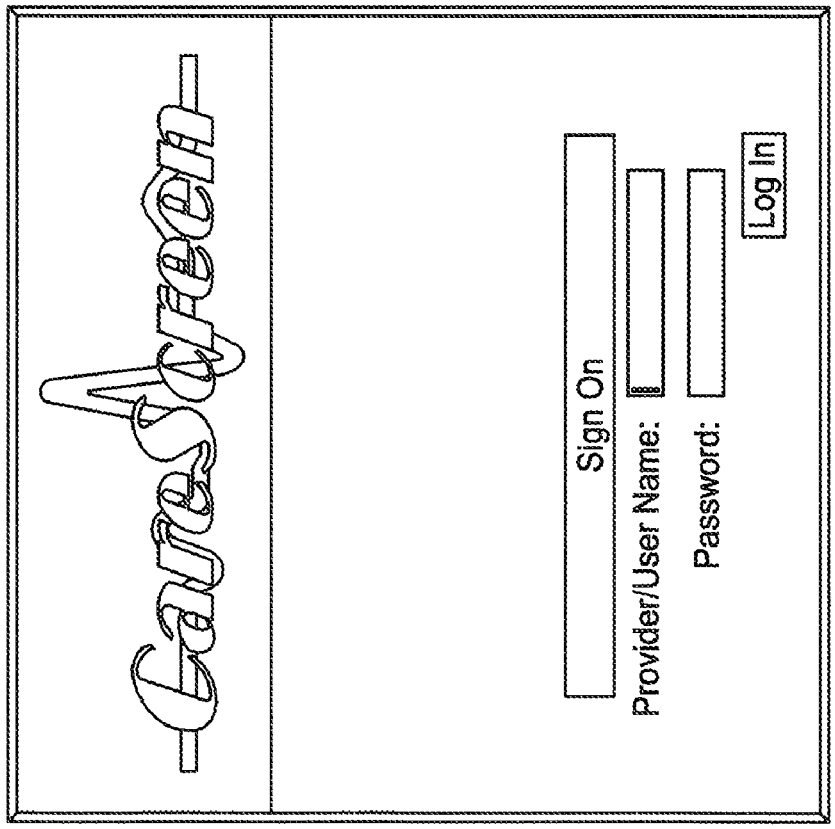
FIG. 7 shows the form used to log-on to the software system.

The preferred method of using the printed encounter form is to have it available for the practitioner's use (see FIG. 5, blocks 502, 504, 506) during the member's office visit (see, generally, FIG. 4, blocks 412, 414 and FIG. 5, blocks 502, 504, 506, 508, 510, 512, 514). For privacy reasons the form is placed face down on the member's chart when not in use. For this reason, the back of the form remains free of any member information. The practitioner completes the form by checking off each item addressed with the member and listed under the heading "Chronic Co-Morbid Condition Diagnoses" on the form (see FIG. 15 and FIG. 5, blocks 508, 510). The form highlights conditions addressed on earlier office visits if information from those visits was entered at that time, or is available from another source. The form also highlights related conditions that should be checked based upon the likelihood that a member presenting with certain conditions will also have related symptoms or conditions worthy of examination. The selection and presentation of additional symptoms and conditions for examination is based upon a subroutine contained in the inventive software and constitutes a principal novel, unique, and highly useful feature of the inventive software. The subroutine uses a table of associations linking certain conditions with others known typically to coexist. In presenting such recommendations to the practitioner, the inventive software enhances the level of care by ensuring that conditions that might otherwise go untreated receive proper attention and care (see highlighted items FIG. 15, e.g.).

The practitioner should also indicate procedures and tests that might be needed as follow-up for the member (see FIG. 5, block 514), and the practitioner can recommend referrals for chronic disease management (see FIG. 14, top right). The practitioner should indicate the proper Current Procedural Technology ("CPT") code under one of the categories marked "Problem Oriented" or "Well Visits" (see FIG. 5, block 512). The primary reason for the visit should be circled. Finally, the practitioner should sign and enter the date of the examination on the form and make an entry indicating the office location (see FIG. 16).

Figure 16:
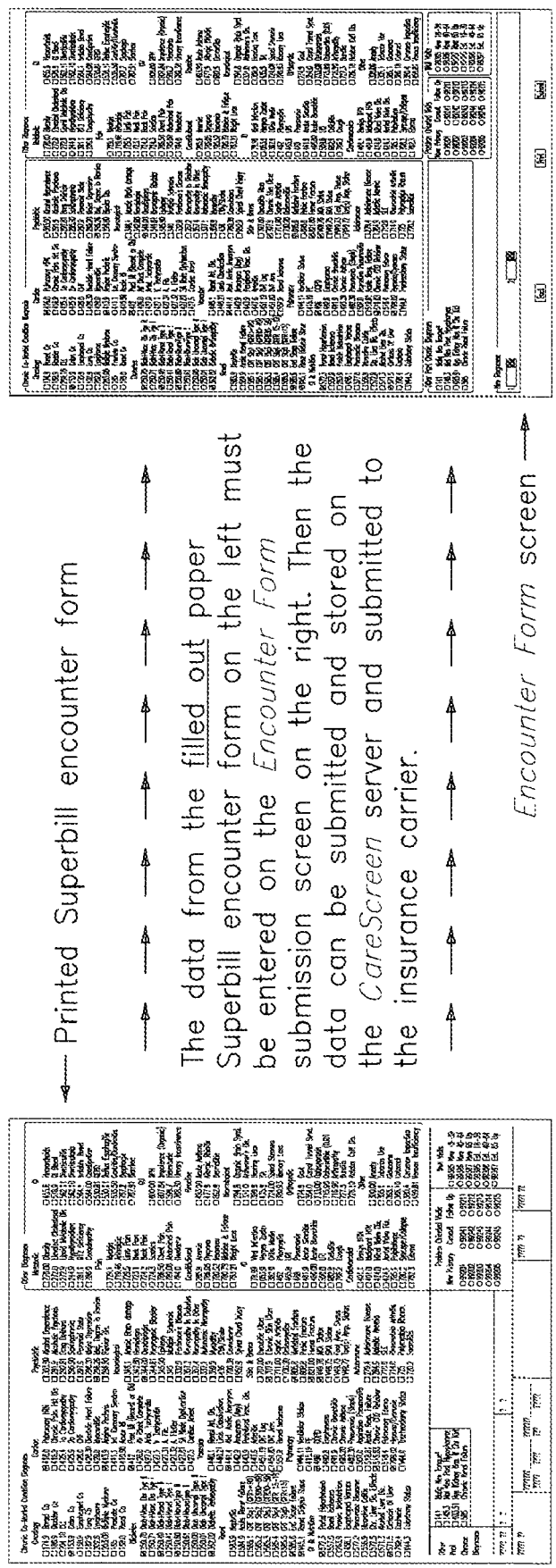
FIG. 16 shows both the printed and executed view; and also the electronic view of the encounter form.

Following the visit, the practitioner or administrative staff must transpose the data from the encounter form into the member database using the "Superbill" encounter form (see FIG. 16). The form is accessed by, as before, opening the "CareScreen member selection screen" (see FIG. 9). The software displays a list of members and using the controls provided on the page (see FIG. 6, blocks 602, 604 and 606), the user navigates to the name of the person shown on the printed encounter form. In this case, instead of clicking on the "print" check box, the user simply executes a single mouse click while pointing to the member's last name (see FIG. 6, block 608). This causes the software to display an electronic copy of the encounter form (see FIGS. 14 and 15). The electronic copy of the encounter form contains the same information presented in the same format as its printed counterpart (see FIG. 6, block 610).

Instead of updating the electronic form after the visit, the practitioner can make entries directly on the electronic form and print it at the end of the examination if desired. There is a look-up feature on the form to aid the practitioner in finding the appropriate International Classification of Disease code ("IDC-9") for new diagnoses if any (see FIG. 15). Once the information is complete (see FIG. 6, blocks 612, 614), the user effects a mouse click on the "submit" control and this causes the "Encounter Review" dialog box to be displayed.

The "Encounter Review" dialog allows the user to change the provider name, encounter date, and location and to select the primary reason for the visit. It also allows the user to return to the electronic encounter form by selecting "Change Diagnoses." Once the review is complete, the user clicks on the Submit Form button (see FIG. 6, block 616) in the "Encounter Review" box (see FIG. 6, blocks 602, 604, 606, 608, 610, 612, 614, 616). This causes the program to save all data from the visit on the secure remote server where it is available for subsequent office visits. The program then returns to the CareScreen Member Selection Screen (see FIG. 9), ready for the next patient.

Applicant's preferred use of a web based SQL server to prompt care providers to check certain conditions based upon patient history from prior office visits, and preferably also using history from other sources, results in more thorough care and enhanced billing. Since the system is set up on a familiar billing format—the so-called "Superbill", it helps to ensure that the service provider's bills and the paperwork submitted to insurance carriers are accurate and complete. The use of Superbills also makes the system easier to learn and to use and improves acceptance by practitioners including those who may have become creatures of habit. In the preferred embodiment, the information is stored on a remote database so it is not subject to being lost or destroyed in the confines of the service provider's office; however, it is possible to run the system on a stand alone computer. The data base security is compliant with Health Insurance Portability and Accountability Act ("HIPPA") regulations.

Applicant's invention can be thought of as a computerized method for aiding medical service providers and their patients. In its broadest form, the method comprises.

a. inputting medical service provider data into a computer system;

b. inputting patient data into the computer system;

c. securely storing the patient data, on the computer system, for later manipulation and for compliance with privacy laws;

d. providing the service provider, shortly before and/or during an encounter with the patient, with a digital version of a Superbill, wherein medical categories on the Superbill have been digitally highlighted to display a medical history of the patient;

e. utilizing the highlighted Superbill during the encounter to ensure the medical service provider:

i. investigates medical conditions of the patient, as prompted by highlights in the Superbill;

ii. exhaustively addresses all the conditions worthy of investigation based on stored patient information; and f. inputting additional patient data, obtained during the encounter, for use in subsequent encounters with the patient and for providing complete billing information.

The method can also include the following steps:

a. accessing the computer system via the Internet.

b. utilizing the additional patient data to invoice a health insurance provider appropriately for all qualified conditions evaluated during the patient encounter.

c. utilizing the additional patient data to invoice a patient appropriately for all qualified conditions evaluated.

d. producing, via the computer system, reports indicating the need for referral encounters were procedures for certain patients, and e. identifying, via the computer system, patients most in need of health care resources.

f. wherein input data is manually entered based solely upon encounters between at single medical service provider, or a plurality of service providers, with a plurality of patients.

It should be understood by those skilled in the art that obvious structural modifications could be made without departing from the spirit or scope of the invention. For example, instead of being web-based, the software could be run directly loaded onto main servers, or standalone workstations, at medical offices or hospitals. Consequently, reference should be made primarily to the appended claims rather than the foregoing description.

What is claimed is:

1. A computerized method for aiding medical service providers and their patients comprising the following steps:
   a. inputting medical service provider data for a patient into a computer system;
   b. inputting patient data into the computer system, wherein the patient data includes medical conditions of the patient which have been identified;
   c. securely storing the patient data, on the computer system, for later manipulation and for compliance with privacy laws;
   d. subsequently providing a medical service provider, during an encounter with the patient, with a digital version of a superbill listing medical categories, wherein:
      i. a plurality of the medical categories listed in the superbill have been digitally highlighted to display the medical conditions of the patient which have been identified previously; and
      ii. a remainder of the medical categories listed in the superbill have not been digitally highlighted;
   e. utilizing the highlighted medical categories in the superbill during the encounter by prompting the medical service provider:
      i. to investigate and address the medical conditions of the patient, during the encounter with the patient, by reviewing the highlighted medical categories in the superbill; and
      ii. to indicate on the superbill all medical conditions of the patient investigated and addressed during the encounter to provide billing information to an insurance carrier;
   f. inputting additional patient data, obtained during the encounter, into the computer system for use in subsequent encounters with the patient and for providing complete billing information; and
   g. wherein the superbill is a standard billing format, used by medical service providers and health insurance carriers, for bills submitted by service providers to the insurance carriers.

2. The method of claim 1 wherein the computer system is accessed via the Internet.

3. The method of claim 1 further comprising:
   a. producing, via the computer system, reports indicating the need for referrals for certain patients, and
   b. identifying, via the computer system, patients needing health care resources.

4. A computerized method for aiding medical service providers and their patients comprising the following steps:
   a. inputting medical service provider data for a patient into a computer system;
   b. inputting patient data into the computer system, wherein the patient data includes medical conditions of the patient which have been identified;
   c. securely storing the patient data, on the computer system, for later manipulation and for compliance with privacy laws;
   d. subsequently providing a medical service provider, during an encounter with the patient, with a digital version of a superbill having listed medical categories, wherein:
      i. a plurality of medical categories listed in the superbill have been digitally highlighted to display the medical conditions of the patient which have been identified previously; and
      ii. a remainder of the medical categories listed in the superbill have not been digitally highlighted;
   e. highlighting additional medical conditions in the superbill which are known typically to coexist with the previously identified medical conditions, whereby the additional highlighting serves to direct the medical service provider's attention to the additional medical conditions;
   f. utilizing the highlighted medical categories in the superbill during the encounter to prompt the medical service provider:
      i. to investigate and address the medical conditions of the patient, during the encounter with the patient, by reviewing the highlighted medical categories in the superbill; and
      ii. to indicate on the superbill all medical conditions of the patient investigated and addressed during the encounter to provide billing information to an insurance carrier;
   g. inputting additional patient data, obtained during the encounter, into the computer system for use in subsequent encounters with the patient and for providing complete billing information; and
   h. wherein the superbill is a standard billing format, used by medical service providers and insurance carriers, for invoices submitted by medical service providers to the insurance carriers.

5. A computerized method for aiding medical service providers and their patients comprising the following steps:
   a. inputting medical service provider data for a patient into a computer system;
   b. inputting patient data into the computer system, wherein the patient data includes at least one medical condition of the patient identified previously;
   c. securely storing the patient data, on the computer system, for later manipulation and for compliance with privacy laws;
   d. subsequently providing a medical service provider, during an encounter with the patient, with a digital version of a superbill having listed categories, wherein:
      i. at least one medical category listed in the superbill has been digitally highlighted to display the at least one medical condition of the patient previously identified; and
      ii. a remainder of the medical categories listed in the superbill have not been digitally highlighted;
   e. utilizing the at least one highlighted medical category in the superbill during the encounter to ensure prompt the medical service provider:
      i. to investigate and address the at least one medical condition of the patient, during the encounter with the patient, by reviewing the at least one highlighted medical category in the superbill; and
      ii. to indicate on the superbill each medical condition of the patient investigated and addressed during the encounter to provide billing information to an insurance carrier;

f. inputting additional patient data, obtained during the encounter, into the computer system for use in subsequent encounters with the patient and for providing complete billing information; and wherein the superbill is a standard billing format, used by medical service providers and insurance carriers, for invoices submitted by medical service providers to the insurance carriers.

6. The method of claim 5 farther comprising:
a. highlighting additional medical conditions known typically to coexist with the at least one previously identified medical condition, whereby the additional highlighting serves to prompt the medical service to review the additional medical conditions.

* * * * *